United States Patent

Teissier et al.

[11] Patent Number: 5,936,131
[45] Date of Patent: Aug. 10, 1999

[54] PROCESS FOR OBTAINING β-HYDROXY AND/OR α,β-UNSATURATED CARBONYL COMPOUNDS

[75] Inventors: Rémy Teissier, Francheville; Maurice Fournier, St-Etienne-de-Cuines, both of France

[73] Assignee: ELF Atochem S,A, Puteaux, France

[21] Appl. No.: 08/808,118

[22] Filed: Feb. 28, 1997

[30] Foreign Application Priority Data

Feb. 29, 1996 [FR] France .................................. 96 02551

[51] Int. Cl.$^6$ ................................................. C07C 45/72
[52] U.S. Cl. ..................... 568/463; 568/388; 568/390; 568/880; 502/341
[58] Field of Search ...................... 568/463, 464, 568/388, 390, 850, 880; 502/80, 85, 341

[56] References Cited

U.S. PATENT DOCUMENTS

| | | |
|---|---|---|
| 4,458,026 | 7/1984 | Reichle . |
| 4,476,324 | 10/1984 | Reichle . |
| 5,144,089 | 9/1992 | Arena ........................................ 568/463 |
| 5,254,743 | 10/1993 | Holmgren et al. . |
| 5,672,764 | 9/1997 | Teissier ................................... 568/388 |

FOREIGN PATENT DOCUMENTS

| | | |
|---|---|---|
| A1-720977 | 7/1996 | European Pat. Off. . |
| WO 92/00266 | 1/1992 | WIPO . |

*Primary Examiner*—Shailendra Kumar
*Assistant Examiner*—Sreeni Padmanabhan

[57] ABSTRACT

The present invention relates to a process for obtaining β-hydroxy carbonyl compounds and/or α,β-unsaturated carbonyl compounds, characterized in that at least one aldehyde or one ketone is brought into contact with a solid catalyst of general formula (I):

$$[(Mg^{2+})_{1-x}(Al^{3+})_x(OH^-)_2]^{x+}[(OH^-)_x]^{x-}(H_2O)_n \qquad (I)$$

with $0.20 \leq x \leq 0.33$ and $n<1$.

20 Claims, No Drawings

PROCESS FOR OBTAINING β-HYDROXY AND/OR α,β-UNSATURATED CARBONYL COMPOUNDS

BACKGROUND OF THE INVENTION

1.1 Technical Field

The present invention relates to a new process for obtaining β-hydroxy carbonyl compounds and/or α,β-unsaturated carbonyl compounds. More particularly its subject-matter is a process for aldolization and/or aldolization-crotonization of an aldehyde and/or of a ketone.

1.2 Description of Related Art

Industrial processes based on the reaction of aldol condensation of aldehydes and of ketones utilize a basic catalyst such as dilute solutions of potassium hydroxide and sodium hydroxide. The separation of these catalysts at the end of the reaction is not, however, easy and requires the addition of acidic solutions, especially sulfuric acid, to convert the catalysts into the corresponding salts. In addition, the removal of salts thus formed, which is necessary for the protection of the environment, is costly for industry.

To overcome the above-mentioned disadvantages the use of solid catalysts has been proposed. Thus, copper oxide supported on a γ-alumina has been described in U.S. Pat. No. 4,739,122 for catalyzing the reaction of mixed aldol condensation between acetone and butanal.

U.S. Pat. No. 5,144,089 discloses a process for liquid-phase aldol condensation, especially the conversion of butanal to 2-ethyl-2-hexenal in the presence of a solid catalyst. The catalyst is a solid solution of magnesium oxide and aluminum oxide, derived from a hydrotalcite and has a specific surface area greater than 250 m²/g.

Titanium dioxide has also been described as catalyst for the aldol condensation reaction in the process for obtaining α,β-unsaturated aldehydes (U.S. Pat. No. 4,316,990).

Catalysis on an ion exchange resin has also been used but without great success, because the resin cannot withstand a temperature higher than 90° C. In addition, once the resin is deactivated, it can no longer be regenerated.

SUMMARY OF THE INVENTION

It has now been found that the above-mentioned disadvantages can be overcome by employing a catalyst of the general formula (I):

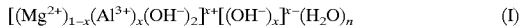

with $0.20 \leq x \leq 0.33$ and $n<1$.

The subject-matter of the invention is therefore a process for obtaining β-hydroxy carbonyl compounds and/or α,β-unsaturated carbonyl compounds. This process is characterized in that at least one aldehyde or one ketone is brought into contact with a solid catalyst of general formula (I):

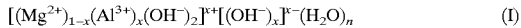

with $0.20 \leq x \leq 0.33$ and $n<1$.

In most cases an aldehyde or a ketone which has at least one hydrogen atom on the carbon α to the carbonyl functional group is employed.

DESCRIPTION OF THE INVENTION

The process according to the present invention preferably consists of reacting, in the presence of a catalyst of the general formula (I), an aldehyde of general formula $R^1$—CHO, in which $R^1$ denotes a linear or branched alkyl radical containing from 1 to 10 carbon atoms with, optionally, at least one compound chosen from another aldehyde of general formula $R^2$—CHO in which $R^2$ denotes a hydrogen atom or a linear or branched alkyl or cyclic radical containing from 1 to 10 carbon atoms or a phenyl radical or a benzyl radical or an aralkyl radical and/or a ketone of general formula $R^5$—CO—$R^6$ in which each of $R^5$ and $R^6$, which are identical or different, denotes a linear or branched alkyl radical containing from 1 to 10 carbon atoms and capable of being joined to each other to form a ring. As used herein, aralkyl is understood to include arylalkyl.

It is also preferred to react a ketone of general formula $R^3$—CO—$R^4$ in which each of $R^3$ and $R^4$, which are identical or different, denotes a linear or branched alkyl radical containing from 1 to 10 carbon atoms, with optionally at least one compound chosen from an aldehyde of general formula $R^2$—CHO in which $R^2$ denotes a hydrogen atom or a linear or branched alkyl or cyclic radical containing from 1 to 10 carbon atoms or a phenyl radical or a benzyl radical or an aralkyl radical, and/or another ketone of formula $R^5$—CO—$R^6$, in which each of $R^5$ and $R^6$, which are identical or different, denotes a linear or branched alkyl radical containing from 1 to 10 carbon atoms and capable of being joined to each other to form a ring, in the presence of a catalyst of general formula (I).

The subject-matter of the present invention is very particularly a process of aldolization and/or aldolization-crotonization of at least one aldehyde or one ketone (with the exclusion of the process of selective aldolization of acetone to diacetone alcohol) in the presence of a catalyst of formula (I).

The process according to the present invention advantageously includes bringing a ketone of general formula $R^3$—CO—$R^4$ and an aldehyde of general formula $R^2$—CHO into contact with a catalyst of formula (I).

The ketone is preferably chosen from those in which $R^3$ or $R^4$ denotes a methyl radical, such as in particular acetone, ethyl methyl ketone or methyl propyl ketone. Acetone is particularly preferred.

The aldehyde is advantageously chosen from methanal, ethanal, propanal, butanal, isobutanal and benzaldehyde. Butanal or isobutanal is preferably employed.

The process advantageously also includes bringing an aldehyde $R^1$—CHO and optionally another aldehyde $R^2$—CHO into contact with the catalyst whose formula (I) is given above.

The aldehyde $R^1$—CHO is advantageously chosen from ethanal, propanal, butanal, isobutanal, pentanal, hexenal and heptenal.

The aldehyde $R^2$—CHO is advantageously chosen from methanal, ethanal, propanal, butanal, isobutanal and benzaldehyde. Methanal, butanal and isobutanal are preferably employed.

Ethanal, butanal or isobutanal is advantageously employed for the process of aldolization and/or aldolization-crotonization of an aldehyde. Butanal is particularly preferred.

The β-hydroxy and α,β-unsaturated carbonyl compounds which are advantageously manufactured according to the process of the present invention are those such as, especially, mesityl oxide, 2-ethyl-2-hexenal, 5-methyl-3-hexen-2-one, 3-hepten-2-one and 2,2',4-trimethyl-3-hydroxypentanal.

The α,β-unsaturated carbonyl compounds obtained in accordance with the process of the present invention can be subjected either to a selective hydrogenation, using known catalysts, to give corresponding saturated carbonyl compounds like aldehydes or ketones which have a higher molecular weight than that or those which are used, or to a total hydrogenation, to give the corresponding saturated alcohols. These aldehydes or ketones or alcohols are employed industrially as synthesis intermediates or as solvents or in the perfumery industry.

The process for obtaining β-hydroxy carbonyl compounds and/or α,β-unsaturated carbonyl compounds according to the present invention can be conducted at a temperature within limits that are also far apart, ranging approximately from 0°C. to approximately 200° C.

In most cases the operation is preferably carried out at a temperature of between approximately 0° C. and approximately 140° C.

A temperature of between approximately 0° C. and approximately 100° C. is more preferably employed.

The pressure at which the operation is carried out is such that the reactants (aldehydes and/or ketones) are in the liquid state at the aldolization or aldolization-crotonization temperature. Although it may be possible to work at a pressure higher than the atmospheric pressure, in most cases it is preferred to operate at atmospheric pressure.

The process according to the invention can be conducted equally well continuously and noncontinuously. The continuous process is preferred industrially.

When operating continuously, the process consists of introducing at least one aldehyde and/or one ketone through a stationary bed or stirred bed of solid catalyst of general formula (I).

The reactants may be introduced separately, or partially or totally premixed, before being introduced into the reactor. They may also be introduced into the reactor either simultaneously or successively. The method of operation depends on their relative reactivity and on the desired final product.

In general, when two aldehydes or two ketones or a ketone and an aldehyde that have different reactivities are brought into contact in the presence of the catalyst of general formula (I), an excess of the less active compound is always employed. The molar ratio of the least active aldehyde or ketone to the more active aldehyde or ketone is in general between approximately 1.2 and approximately 12 and preferably between approximately 1.5 and approximately 8.

When operating noncontinuously, the quantity of catalyst employed relative to the total charge of reactants introduced into the reactor is in general between approximately 0.5% and approximately 20% by mass, and preferably between approximately 2% and approximately 15% by mass.

A mass ratio of catalyst employed to the total charge of reactants introduced of between approximately 3% and approximately 10% is particularly preferred.

The catalyst of general formula (I):

$$[(Mg^{2+})_{1-x}(Al^{3+})_x(OH^-)_2]^{x+}[(OH^-)_x]^{x-}(H_2O)_n \qquad (I)$$

which has a value of n that can range from about 0.48 to about 0.75 is in most cases employed in the process according to the present invention.

A catalyst of general formula (I) which advantageously has a value of n which ranges from about 0.48 to about 0.61 is chosen, such as especially meixnerite of formula:

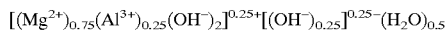

The catalyst of general formula (I) can be prepared in accordance with the method described by G. Mascolo and O. Marino in Mineralogical Magazine, March 1980, Vol.43, p. 619.

This method of preparation consists of suspending alumina gel and MgO, obtained by calcining basic magnesium carbonate at 650° C., in distilled water in a closed TEFLON receptacle, with stirring, for a week at 80±1° C. The suspension is next filtered with protection against $CO_2$ and finally the solid collected is dried over silica gel.

This catalyst can also be prepared by hydration of a magnesium aluminum double oxide $Mg_{1-x}Al_xO_{1+x}$ in the absence of $CO_2$. The hydration is performed with water either in the liquid phase or in the vapor phase. The mixed double oxide may be either a commercial product or one obtained by calcining hydrotalcites, with a value of x that can range from 0.2 to 0.33, at a temperature lower than 800° C.

After the hydration stage in accordance with either of the methods described above, the solid may be dried either by evaporation at reduced pressure at a temperature lower than 60° C. or by rinsing with a water-miscible solvent like, for example, acetone.

To prepare the catalyst of general formula (I) a commercial double oxide is advantageously chosen, and preferably that from the Japanese company Kyowa, known as KW 2000 which has a value of x of about 0.3.

In most cases the double oxide is hydrated in the liquid phase and the solid thus obtained is advantageously rinsed with a water-miscible solvent and preferably with acetone.

DESCRIPTION OF THE PREFERRED EMBODIMENTS

The invention will be understood better from the following nonlimiting examples:

EXAMPLE 1

Preparation of catalyst.

The mixed double oxide KW 2000 which has the following characteristics is hydrated with water in the liquid phase:

Chemical formula: 4.5 $MgO.Al_2O_3$ (x=0.3077)

Apparent density: 44 ml/10 g

Appearance: odorless fine white powder

BET surface area=172 $m^2/g$

Mean particle size: 70 μm.

Absorbent property: absorbs at most 70–80 parts of water per 100 parts of KW 2000.

Thus, 6 grams of KW 2000 are added with stirring to 200 ml of decarbonated water (ion-exchanged and then boiled water). The mixture is stirred for 3 hours and then the solid is separated off. The solid isolated is next rinsed several times with acetone before being stored with protection against $CO_2$. 9 g of solid are obtained of general formula (I) where x has the value 0.3077 and which has a crystal structure of the hydrotalcite or meixnerite type.

EXAMPLE 2

4.9 g of the catalyst of Example 1, followed by 37 g of acetone, are introduced at ambient temperature into a thermostated stirred reactor purged with a stream of nitrogen. The charge is then heated with stirring to 50° C. over 30 minutes. 100 g of a mixture containing 75% by weight of acetone and 25% by weight of isobutanal are then introduced over two hours. After the end of the introduction of the mixture the reaction is allowed to proceed for 90 minutes at 50° C. At the end of the reaction the catalyst is filtered off and the final solution is analyzed by gas phase chromatography. The chromatograph employed is a Perkin-Elmer 8420 equipped with an FID detector, a J & W DB 1701 type capillary column 25 μm in diameter and 30 m in length. The temperature of the injector is 280° C. and that of the detector is 175° C. The injector comprises a split of 60 ml/min. The oven is programmed with a gradient of 3° C./min from the initial temperature of 80° C. to the final temperature of 200° C.

Chromatographic analysis of the final solution gives an isobutanal conversion of 98%, a selectivity for 5-methyl-4-hydroxy-2-hexanone of 34% and a selectivity for 5-methyl-3-hexen-2-one of 45%. The total selectivity for β-hydroxy and α,β-unsaturated carbonyl compounds is 79%.

EXAMPLE 3

The procedure is identical to Example 2 but butanal is employed instead of isobutanal. The results obtained at the end of the reaction are:

Butanal conversion 96%

Selectivity for 4-hydroxy-2-heptanone=41%

Selectivity for 3-hepten-2-one=30%

Total selectivity for β-hydroxy and α,β-unsaturated carbonyl compounds=71%.

EXAMPLE 4 (COMPARATIVE)

The procedure is identical to Example 3 but 4.9 g of the commercial double oxide KW 2000 are employed instead of the catalyst in Example 1. The results obtained at the end of the reaction are:

Butanal conversion=7%

Selectivity for 4-hydroxy-2-heptanone=37%

Selectivity for 3-hepten-2-one=5%

Total selectivity for β-hydroxy and α,β-unsaturated carbonyl compounds=42%.

EXAMPLE 5 (COMPARATIVE)

The procedure is identical to Example 2 but 4.9 g of the commercial double oxide KW 2000 are employed instead of the catalyst of Example 1. The results obtained at the end of the reaction are:

Isobutanal conversion=7%

Selectivity for 5-methyl-4-hydroxy-2-hexanone=40%

Selectivity for 5-methyl-3-hexen-2-one=10%

Total selectivity for β-hydroxy and α,β-unsaturated carbonyl compounds=50%.

EXAMPLE 6 (COMPARATIVE)

The procedure is identical to Example 2 but 10 g of 2N methanol sodium hydroxide, that is 0.8 g of pure sodium hydroxide, are employed instead of the catalyst of Example 1.

The results obtained at the end of the reaction are:

Isobutanal conversion=99%

Selectivity for 5-methyl-4-hydroxy-2-hexanone=13%

Selectivity for 5-methyl-3-hexen-2-one=6%

Total selectivity for β-hydroxy and α,β-unsaturated carbonyl compounds=19%.

EXAMPLE 7

5g of the catalyst of Example 1, followed by 100 g of butanal, are introduced at ambient temperature into a thermostated, stirred 0.5-liter reactor purged with a stream of nitrogen. The charge is then heated to 75° C. over 30 minutes and left stirred for 3 hours. At the end of the reaction the catalyst is filtered off and the final solution is analyzed by gas phase chromatography in the same way as in Example 2.

A butanal conversion of 77%, a selectivity for 2-ethyl-2-hexenal of 57% and a selectivity for 2-ethyl-3-hydroxy hexanal of 10% are obtained. The total selectivity for β-hydroxy and α,β-unsaturated carbonyl compounds is 67%.

EXAMPLE 8, (COMPARATIVE)

The procedure is identical to Example 7, but the commercial double oxide KW 2000 is employed instead of the catalyst of Example 1.

At the end of 3 hours a butanal conversion of 8% and a selectivity for 2-ethyl-2-hexenal of 30% and a selectivity for 2-ethyl-3-hydroxy hexanal of 50% are obtained. The total selectivity for β-hydroxy and α,β-unsaturated carbonyl compounds is 80%.

What is claimed is:

1. A process for obtaining a compound which is a member of the group consisting of a β-hydroxy carbonyl compound, a α,β-unsaturated carbonyl compound, and mixtures thereof, comprising the step of bringing at least one aldehyde or one ketone into contact with a solid catalyst of general formula (I):

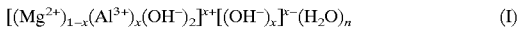

$$[(Mg^{2+})_{1-x}(Al^{3+})_x(OH^-)_2]^{x+}[(OH^-)_x]^{x-}(H_2O)_n \qquad (I)$$

with $0.20 \leq x \leq 0.33$ and $n<1$, and wherein the total selectivity of the β-hydroxy carbonyl compound and the α,β-unsaturated carbonyl compound is 67% or higher, and when butanal or isobutanal is used in the process, a conversion percentage of butanal or isobutanal is 77% or higher.

2. The process according to claim 1, characterized in that at least e aldehyde or one ketone has a hydrogen atom on the carbon to the carbonyl functional group.

3. The process according to claim 1, characterized in that the aldehyde has the general formula $R^1$—CHO, in which $R^1$ denotes a linear or branched alkyl radical containing from 1 to 10 carbon atoms.

4. The process according to claim 3, characterized in that the aldehyde is reacted with at least one compound chosen from the group consisting of:

a second aldehyde, wherein said second aldehyde is of the general formula $R^2$—CHO in which $R^2$ denotes a hydrogen atom, a linear or branched alkyl or cyclic radical containing from 1 to 10 carbon atoms, a phenyl radical, a benzyl radical, or an arylalkyl radical; and a ketone, wherein said ketone is of the general formula $R^5$—CO—$R^6$ in which each of $R^5$ and $R^6$, which are identical or different, denotes a linear or branched alkyl radical containing from 1 to 10 carbon atoms and capable of being joined to each other to form a ring.

5. The process according to claim 1, characterized in that the ketone has the general formula $R^3$—CO—$R^4$, in which each of $R^3$ and $R^4$, which are identical or different, denotes a linear or branched alkyl radical containing from 1 to 10 carbon atoms.

6. The process according to claim 5, characterized in that the ketone is reacted with at least one compound chosen from the group consisting of:

an aldehyde of, wherein said aldehyde is of the general formula $R^2$—CHO in which $R^2$ denotes a hydrogen atom, a linear or branched alkyl or cyclic radical containing from 1 to 10 carbon atoms, a phenyl radical, a benzyl radical or an arylalkyl radical; and a second ketone, wherein said second ketone is of the general formula $R^5$—CO—$R^6$ in which each of $R^5$ and $R^6$, which are identical or different, denotes a linear or branched alkyl radical containing from 1 to 10 carbon atoms and capable of being joined to each other to form a ring.

7. The process according to claim 3, characterized in that the aldehyde of general formula $R^1$—CHO is ethanal, propanal, butanal, isobutanal, pentanal, hexanal or heptanal.

8. The process according to claim 7, characterized in that the aldehyde is butanal or isobutanal.

9. The process according to claim 4, characterized in that the aldehyde of general formula $R^2$—CHO is methanal, ethanal, propanal, butanal, isobutanal or benzaldehyde.

10. The process according to claim 9, characterized in that the aldehyde is methanal, butanal or isobutanal.

11. The process according to claim 5, characterized in that the ketone of general formula $R^3$—CO—$R^4$ is acetone, ethyl methyl ketone or methyl propyl ketone.

12. The process according to claim 11, characterized in that the ketone is acetone.

13. The process according to claim 1, characterized in that the catalyst of general formula (I) has a value of n ranging from about 0.48 to about 0.75.

14. The process according to claim 13, characterized in that the value of n ranges from about 0.48 to about 0.61.

15. The process according to claim 1, characterized in that the process is carried out at a temperature of between 0° C. and 200° C.

16. The process according to claim 15, characterized in that the temperature is between 0° C. and 140° C.

17. The process according to claim 16, characterized in that the temperature is between 0° C. and 100° C.

18. The process according to claim 1, whereby a product of said process is 4-hydroxy-2-heptanone, 3-hepten-2-one or mixtures thereof.

19. The process according to claim 1, whereby a product of said process is 5-methyl-4-hydroxy-2-hexanone, 5-methyl-3-hexen-2-one or mixtures thereof.

20. The process according to claim 1, whereby a product of said process is 2-ethyl-3-hydroxy hexanal, 2-ethyl-2-hexenal or mixtures thereof.

* * * * *